US009044262B2

(12) United States Patent
Harris (10) Patent No.: US 9,044,262 B2
(45) Date of Patent: *Jun. 2, 2015

(54) FOLLICULAR EXTRACTION METHOD (75) Inventor: James A. Harris, Denver, CO (US)

(73) Assignee: HSC DEVELOPMENT LLCCO (US)

( * ) Notice: Subject to any disclaimer, the term of this patent is extended or adjusted under 35 U.S.C. 154(b) by 472 days.

This patent is subject to a terminal disclaimer.

(21) Appl. No.: 13/474,163

(22) Filed: May 17, 2012

(65) Prior Publication Data
US 2012/0226290 A1 Sep. 6, 2012

Related U.S. Application Data (60) Continuation of application No. 12/331,057, filed on Dec. 9, 2008, now Pat. No. 8,211,117, which is a division of application No. 11/102,550, filed on Apr. 8, 2005.

(60) Provisional application No. 60/591,786, filed on Jul. 28, 2004, provisional application No. 60/560,397, filed on Apr. 8, 2004.

(51) Int. Cl.
A61B 17/50 (2006.01)
A61B 17/3205 (2006.01)
A61B 17/34 (2006.01)
A61F 2/10 (2006.01)
A61B 17/00 (2006.01)
(Continued)

(52) U.S. Cl.
CPC ....... *A61B 17/32053* (2013.01); *A61B 17/3468* (2013.01); A61B 2017/00752 (2013.01); A61B 2017/306 (2013.01); A61B 2017/320044 (2013.01); *A61F 2/10* (2013.01)

(58) Field of Classification Search
CPC ............... A61B 17/32053; A61B 2017/00752; A61B 17/3468; A61B 2017/306
USPC .......................................... 606/133, 187, 131
See application file for complete search history.

(56) References Cited

U.S. PATENT DOCUMENTS 1,433,340 A 10/1922 Clark
3,512,519 A 10/1967 Hall
3,998,230 A 12/1976 Miller
(Continued)

FOREIGN PATENT DOCUMENTS

EP 1293167 A2 3/2003
WO 9947059 9/1999
WO 02065919 A1 8/2002

OTHER PUBLICATIONS

William R. Rassman et al., Follicular Unit Extraction: Minimally Invasive Surgery for Hair Transplantation, Blackwell Publishing, Inc. ISSN: 1076-0512/02/. 28: pp. 720-728. Dermatol Surg. 2002.
(Continued)

*Primary Examiner* — Kathleen Holwerda
*Assistant Examiner* — Sarah Simpson
(74) *Attorney, Agent, or Firm* — Marsh, Fischmann & Breyfogle LLP; Lena I. Vinitskaya (57) ABSTRACT A method for the extraction of follicular units from a donor area on a patient. The method includes scoring the outer skin layers with a sharp punch, and then inserting a blunt punch into the incision to separate the hair follicle from the surrounding tissue and fatty layer. The method will significantly decrease the amount of follicular transection and increase the rate at which follicular units can be extracted.

37 Claims, 8 Drawing Sheets (51) Int. Cl.
  *A61B 17/30* (2006.01)
  *A61B 17/32* (2006.01)

(56) References Cited

U.S. PATENT DOCUMENTS

| | | | |
|---|---|---|---|
| 4,099,518 A | | 7/1978 | Baylis et al. |
| 4,122,855 A | | 10/1978 | Tezel |
| 4,160,453 A | * | 7/1979 | Miller ............... 606/187 |
| 4,476,864 A | | 10/1984 | Tezel |
| 4,873,991 A | | 10/1989 | Skinner |
| 5,019,091 A | | 5/1991 | Porat et al. |
| 5,036,860 A | | 8/1991 | Leigh et al. |
| 5,183,053 A | | 2/1993 | Yeh et al. |
| 5,269,316 A | | 12/1993 | Spitalny |
| 5,341,816 A | | 8/1994 | Allen |
| 5,417,683 A | | 5/1995 | Shiao |
| 5,439,475 A | | 8/1995 | Bennett |
| 5,507,765 A | | 4/1996 | Mott |
| 5,578,054 A | | 11/1996 | Arnold |
| 5,693,064 A | | 12/1997 | Arnold |
| 5,707,362 A | | 1/1998 | Yoon |
| 5,725,553 A | | 3/1998 | Moenning |
| 5,766,177 A | | 6/1998 | Lucas-Dean et al. |
| 5,782,851 A | | 7/1998 | Rassman |
| 5,792,163 A | | 8/1998 | Hitzig |
| 5,792,169 A | | 8/1998 | Markman |
| 5,817,120 A | | 10/1998 | Rassman |
| 5,827,199 A | | 10/1998 | Alexander |
| 5,857,981 A | | 1/1999 | Bucalo et al. |
| 5,885,226 A | | 3/1999 | Rubinstein et al. |
| 5,895,403 A | * | 4/1999 | Collinsworth ............... 606/184 |
| 5,922,000 A | | 7/1999 | Chodorow |
| 5,989,273 A | | 11/1999 | Arnold |
| 6,059,807 A | | 5/2000 | Boudjema |
| 6,080,175 A | | 6/2000 | Hogendijk |
| 6,228,039 B1 | | 5/2001 | Binmoeller |
| 6,315,737 B1 | | 11/2001 | Skinner |
| 6,416,484 B1 | | 7/2002 | Miller et al. |
| 6,461,369 B1 | | 10/2002 | Kim |
| 6,572,625 B1 | | 6/2003 | Rassman |
| 6,579,281 B2 | | 6/2003 | Palmer et al. |
| 6,616,683 B1 | | 9/2003 | Toth et al. |
| 6,641,564 B1 | | 11/2003 | Kraus |
| 7,156,856 B2 | | 1/2007 | Feller |
| 7,172,604 B2 | * | 2/2007 | Cole ............... 606/131 |
| 2003/0097079 A1 | | 5/2003 | Garcia |
| 2003/0097144 A1 | | 5/2003 | Lee |
| 2004/0116942 A1 | * | 6/2004 | Feller ............... 606/133 |
| 2004/0193203 A1 | | 9/2004 | Pak et al. |
| 2004/0220589 A1 | | 11/2004 | Feller |
| 2005/0203545 A1 | | 9/2005 | Cole |
| 2005/0245952 A1 | * | 11/2005 | Feller ............... 606/170 |

OTHER PUBLICATIONS

European Office Action dated Dec. 2, 2011 in corresponding European Patent Application No. EP 05 776 621.4.
European Examination Report dated Nov. 12, 2010 in corresponding European Patent Application No. EP 05 776 621.4.
Supplementary European Search Report issue Jun. 22, 2010 in corresponding European Patent Application No. EP 05 776 621.4.
Notice of Rejection dated Jun. 15, 2010 (with English translation) from corresponding Japanese Patent Application No. 2007-507527.
Korean Office Action issued on Apr. 27, 2009 (with English translation) in corresponding Korean Patent Application No. 10-2006-7022930.
U.S. Office Action issued on May 12, 2010 for U.S. Appl. No. 11/565,553 by Cole.
Response to Office Action dated Aug. 12, 2010 for U.S. Appl. No. 11/565,553 by Cole.
Non-Final Office Action mailed Oct. 15, 2014, in connection with commonly assigned U.S. Appl. No. 11/102,550, (10 pages).
Examination Report from the European Patent Office dated Apr. 19, 2011 in corresponding European Patent Application No, EP 05776621.4 (4 pages).

\* cited by examiner

FOLLICULAR EXTRACTION METHOD

CROSS-REFERENCE TO RELATED APPLICATIONS

This application claims priority as a continuation application to U.S. patent application Ser. No. 12/331,057, filed Dec. 9, 2008, which claims priority as a divisional application to U.S. patent application Ser. No. 11/102,550, filed on Apr. 8, 2005, which claims priority to U.S. Provisional Application No. 60/560,397, filed on Apr. 8, 2004, and to U.S. Provisional Application No. 60/591,786, filed on Jul. 28, 2004. The disclosure of each of these applications is incorporated herein by reference in its entirety.

BACKGROUND OF THE INVENTION

1. Field of the Invention

The present invention relates to a method and device for the extraction of hair grafts from the donor area of a patient for subsequent transplantation to a recipient area. More specifically, the present invention relates to a method and device for the extraction of follicular hair units that decreases the follicular transection rate and improves the yield of transplantable follicular units.

2. Description of Related Art

The basic process of hair transplantation is to remove hair from the side and back fringe areas (donor areas) of the patient's head, and move it to the bald area (recipient area). Historically, 4 mm diameter plugs were utilized as the donor plug; this was followed by mini-grafts (smaller plugs), and finally by follicular units grafts (FUG's). FUG's are naturally occurring aggregates of 3-5 closely spaced hair follicles. The FUG's are distributed randomly over the surface of the scalp.

In the foregoing processes, a linear portion of the scalp is removed from the donor area by dissection with a scalpel. Some follicles are invariably transected during this process, damaging the follicles. In addition to some follicular damage, the removal of this donor strip will always result in a scar. In addition to the scar, there is usually a degree of moderate pain for several days and a sensation of tightness for 6-8 weeks following the procedure. Multiple procedures will result in multiple scars and thinning of the hair above and below the scar. If the pliability or laxity of the scalp is miscalculated, and a strip that is too wide is removed, this procedure has the potential to create a wide, unsightly scar because of the tension required to close the wound. Sometimes the resulting scar can be difficult to hide or disguise, causing a significant cosmetic deformity.

FUG's are dissected from a donor strip by several technicians using operating microscopes. Often the best technicians can produce approximately 250 to 300 grafts per hour, and an average technician produces closer to 200 grafts per hour. The FUG's are sorted into groups based upon the number of hairs contained in the FUG. The best technicians will have a transection rate of from about 2% to 5%.

Recently, Dr. William Rassman and Dr. Robert Bernstein disclosed a technique, called follicular unit extraction (FUE), whereby follicular units were extracted from the donor area without the need to create a linear incision with a scalpel. This was accomplished by using a sharp 1 mm diameter punch to make an incision into the epidermis and dermis, and then removing the follicular unit from the surrounding skin with forceps. Their findings suggested that some follicles were easily removed; others had a significant tendency to shear in the process. By their research, a good candidate was defined as one who experienced less than 20% shearing, and only about 25% of the patients tested were considered good candidates by their shearing test. This test is called the FOX (FOllicular eXtraction) test.

The foregoing procedure is technically difficult, as the penetration depth and penetration angle is difficult to control. If the sharp punch penetrates too deeply or at the incorrect angle there is a good chance of transecting the follicular unit. This method has not been widely adopted due to the problems of transection, difficulty removing the grafts, the time required to produce the grafts, and the low percentage of potential candidates.

Dr. John Cole, an expert in FUE, devised a device that limits the depth of the sharp punch to just below the attachment of the arrector pili muscle (presumably responsible for tethering the FUG to the deeper tissues and causing shearing during extraction), and increases the number of viable grafts produced. He has called his procedure the FIT, or Follicular Isolation Technique. He reports on his website that he has produced and transplanted up to 1200 grafts in one day. It is not believed that the time required to accomplish this has been more accurately reported.

The dissection of grafts from the scalps of African Americans and those with a high percentage of gray or white hairs is particularly problematic. The African American's follicles typically have a high degree of curl or curve, making the dissection difficult and prone to high transection rates. The follicles of white or gray hair are all but invisible, even under the microscope, making them prone to a high rate of transection as well.

There remains a need for a follicular extraction method and related device that reduces the amount of follicular transection and increases the follicular extraction rate.

SUMMARY OF THE INVENTION

To address the problems associated with standard follicular unit production and the current FUE methodology, the present invention provides a method and device to diminish or even eliminate the shortcomings of the existing technology. The method and device can be used by the uninitiated with a degree of success similar to a trained individual.

The method of the present invention first involves the use of a sharp scoring punch to score (incise) the skin to a limited depth of from about 0.3 mm to about 1.5 mm. As used herein, the term sharp is defined as having the capability to cut or incise the skin surface with relative ease by virtue of a thin keen edge. The scoring punch can have a diameter of, for example, about 1 mm (inner diameter). The scoring punch is then removed. Incising to this limited depth drastically reduces the risk of transecting the follicles because of the geometry of the follicle and the limited depth of the incision. This scoring step is followed by the placement of a blunt punch, referred to herein as the "dissecting" punch, into the incision created by the scoring punch. As used herein, blunt is defined as having a dull or rounded edge and being unable to easily cut or incise by virtue of the dull edge. The dissecting punch can have an inside diameter of about 1 mm and can have a length of from about 4 mm to about 6 mm.

The dissecting punch can be rotated slightly and pushed into the skin. Typically the operator feels a "popping" sensation as the leading edge of the dissecting punch goes past the more dense tissues. The graft (follicular unit) formed by the foregoing steps is then removed from the skin, such as with forceps. The blunt aspect of the dissecting punch advantageously reduces transection of follicles preferably to less than 10%, by guiding the group of follicles into the lumen of the punch without shearing the follicles.

A device is also provided according to the present invention to facilitate the implementation of the foregoing method. In one embodiment, the device includes at least two basic components. One component is a sharp scoring punch preferably having an inner diameter of from about 0.7 mm to 1.0 mm but may be smaller or larger, that is housed in a device that limits the depth of insertion, such as to from about 0.3 mm to about 1.5 mm. Once the incision is made, a blunt dissecting punch is activated by a slide mechanism and is inserted into the incision and through the remainder of the skin, without advancing the scoring punch. The blunt dissecting punch can have an inside diameter that is fractionally larger than the outside diameter of the scoring punch.

According to one aspect, the device can include a mechanism to rotate the scoring and dissecting punches without the need to rotate the entire instrument. According to another aspect, a mechanism is included to move the dissecting punch rapidly through the skin layers. According to yet another aspect, a component is included in the device to remove the graft from the skin after the dissecting punch has performed its function.

According to one aspect, the device is a "powered" device utilizing a power source selected from the group of electricity (AC or DC), air (pneumatic), suction, or mechanical power. The powered device advantageously enables the mechanization of the scoring and dissecting functions, thereby relieving stress on the operator.

According to another embodiment, the device includes an elongate handle having a dissecting punch and a scoring punch disposed at opposite ends of the handle.

The method and device according to the present invention can provide value to both the patient and physician. Some of the benefits are as follows:

Patient Benefits
Reduce follicular transection, thus extracting more hair to transplant
Increase donor capability by 50% to 80% (no longer limited by scalp laxity)
Decrease post-operative pain
Speed healing
No visible scarring
Possible faster graft growth
African American and gray haired patients will benefit significantly from less follicle damage
Physician Benefits
Decrease follicular transection
More exact planning for the number of grafts required
Ability to select certain FUG's (i.e., more 4 hair FUG's than 2 hair FUG's to create density or more 1 hair FUG's for the visible hairline)
Decrease number of staff (FUG's can be obtained by physician alone, or by minimal number of qualified staff after limited training)
The ability to obtain grafts from African American and gray haired patients with confidence and minimal transection
The possibility of decreasing overhead and need for technical equipment (e.g., microscopes for graft dissection)
The possibility of decreasing the price per graft and enlarge the potential market
Marketing advantages to physicians offering superior patient outcomes from advanced technology and instrumentation These and other advantages of the present invention will become apparent to those of ordinary skill in the art upon consideration of the following description of the invention.

DESCRIPTION OF THE INVENTION

FIG. 1 schematically illustrates a follicular extraction technique according to the prior art, as developed by Dr. William Rassman and Dr. Robert Bernstein. See, for example, Rassman et al., *Dermatologic Surgery* 2002; 28:720-728. Referring to FIG. 1(a), the patient's skin includes a fatty layer 102, a dermis layer 104, and an epidermis layer 106. Within a donor area, a follicular unit 108 consisting of two hair follicles 110 and 112 extends through the dermis 104 and epidermis 106 layers and is anchored in the fatty layer 102. It will be appreciated by those skilled in the art that follicular unit can include more or less than two hair follicles.

Figure 1A:
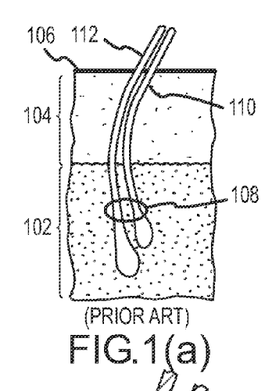
FIG. 1 illustrates a follicular extraction method according to the prior art.
Figure 1B:
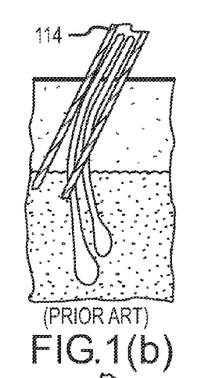
Figure 1C:
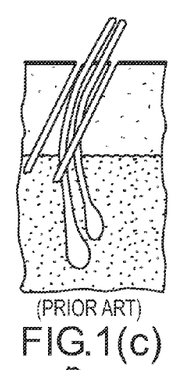
Figure 1D:
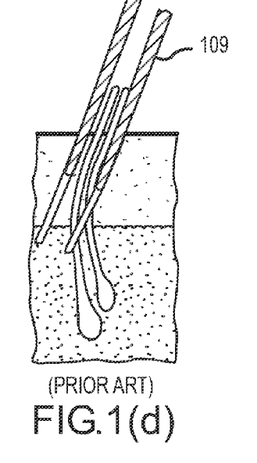
Figure 1E:
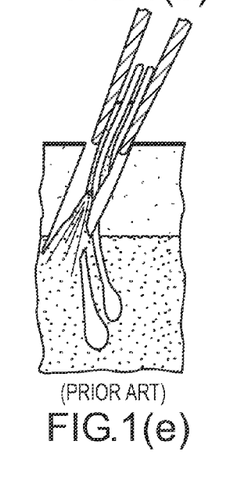
Figure 1F:
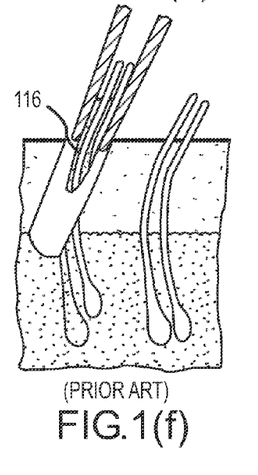

During this follicular extraction technique, the operator aligns a sharp punch 114 substantially parallel with the protruding hairs, and the punch 114 is pushed into the skin with sufficient force such that the sharp edge of the punch 114 extends downwardly through the epidermis 106 and dermis 104 layers (FIG. 1(b). However, as is illustrated in FIG. 1(c), the hair follicles 110 and 112 are transected by the punch 114 if the hair follicles are not substantially parallel through the layers. The operator then removes the follicular unit 116 (FIGS. 1(d), 1(e), and 1(f)) using forceps 109 or a similar device. However, the removed follicular unit 116 is severed and is not useful for transplantation (FIG. 1(f)).

FIG. 2 illustrates a follicular extraction method according to the present invention. Generally, the method of the present invention includes a two-step technique for the preparation of the follicular unit for extraction. The first step scores the skin surrounding the follicular unit and the second step separates the follicular unit from the surrounding tissue and fat in the form of a follicular unit plug without shearing the hair follicles.

Figure 2A:
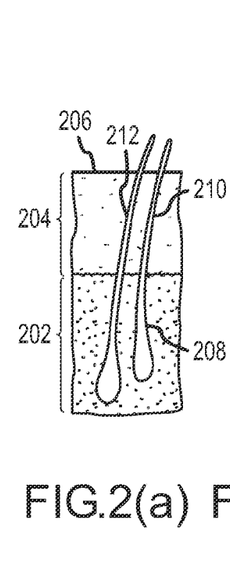
FIG. 2 illustrates a follicular extraction method according to an embodiment of the present invention.

Referring to FIG. 2(a), the patient's skin includes a fatty layer 202, dermis 204, epidermis 206, and a follicular unit 208. The follicular unit consists of two hair follicles, 210 and 212, extending through the dermis and epidermis, and anchored in the fatty layer 202.

Figure 2B:
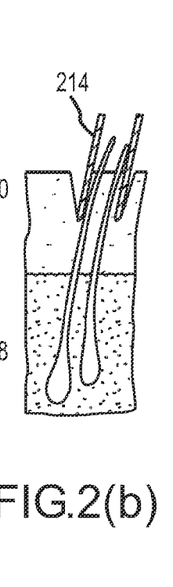

The method of the present invention includes the use of a sharp scoring punch 214 (FIG. 2(b)). The sharp scoring punch 214 includes a cutting edge that is preferably circular in cross-section and preferably has an inner diameter of at least about 0.1 mm and not greater than about 1.1 mm. According to one embodiment, the cutting edge of the scoring punch 214 has an inner diameter of from about 0.7 mm to about 1.0 mm.

The cutting edge of the scoring punch has a sufficient sharpness to cut through the epidermis 206, dermis 204 and fatty layer 202 with relative ease, as is known to those skilled in the art. An example is the 1 mm Dermal Biopsy Punch available from Miltex, Inc., Bethpage, N.Y.

The operator aligns the sharp scoring punch 214 approximately parallel to the hairs 210 and 212 protruding from the epidermis 206 with the protruding hairs being disposed within the lumen of the scoring punch 214. The operator then applies a limited amount of force to the scoring punch 214 such that the scoring punch cuts through the epidermis 206 and scores (partially cuts through) the upper dermis 204, preferably to a total depth of not greater than about 1.5 mm, such as from about 0.3 mm to about 1.5 mm. The sharp scoring punch 214 should be inserted to a depth sufficient to score the skin and upper dermis but not so deep as to risk transection of the follicles. The sharp scoring punch 214 is then removed.

Figure 2C:
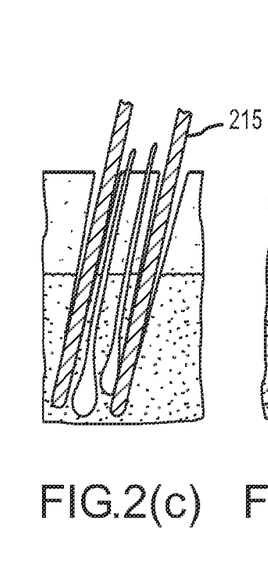
Figure 2D:
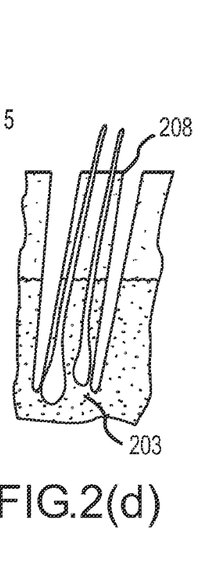
Figure 2E:
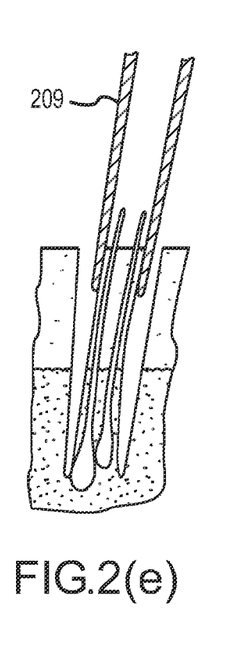
Figure 2F:
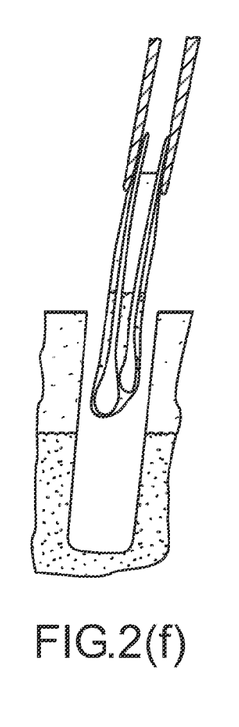

As is illustrated by FIG. 2(c), a blunt dissecting punch 215 that is less sharp than the scoring punch is then placed into the scored incision created by the scoring punch 214. The blunt dissecting punch 215 has an inner diameter that is fractionally larger than the outer diameter of the scoring punch 214, whereby the dissecting punch 215 can readily advance through the incision created by the scoring punch 214. The blunt dissecting punch 215 is less sharp than the scoring punch 214, and the leading edge of the dissecting punch 215 is such that the probability of shearing a hair follicle (e.g., hair follicle 210) is very low. However, the dissecting punch 215 is capable of advancing through the softer dermis 204 and fatty layer 202 without overdue pressure being applied by the operator.

The dissecting punch 215 is advanced through the dermis 204 and the fatty layer 202 to a depth that is sufficient to enable the subsequent removal of the follicular unit 208 in the form of a follicular unit plug (i.e., the follicular unit and immediate surrounding tissue) without substantially damaging the follicular unit 208. Accordingly, the dissecting punch 215 penetrates to a depth that is deeper than the insertion depth of the scoring punch 214 and can be fully inserted through the dermis layer 204 and into the fatty layer 202. According to one embodiment, the dissecting punch 215 is inserted to a total depth of at least about 1.5 mm and not greater than about 8 mm, such as from about 4 mm to about 7 mm (FIG. 2(c)). In one embodiment, the dissecting punch 215 is inserted to a depth of not greater than about 5 mm. This bluntly separates the fibrous attachments surrounding the follicular unit 208, leaving it attached only at its base 203 (FIG. 2(d)). The surgeon then removes the follicular unit 208 from the skin using forceps 209, or a similar device. The follicular unit 208 is removed intact and is ready for implantation at a recipient site.

It will be appreciated by those of ordinary skill in the art that the scoring punch 214 and the dissecting punch 215 can be fabricated from materials normally used for such purposes, such as rigid or semi-rigid materials and the like, particularly metals. It is preferred that the cross-section of each of the scoring punch and the dissecting punch is circular for a variety of reasons, including that a circular cross-section enables the operator to twist (rotate) the punch to facilitate movement into and through the various skin layers. However, other cross-sections may be useful, such as the elliptical biopsy punch disclosed by Yeh et al. in U.S. Pat. No. 5,183,053, which is incorporated herein by reference in its entirety.

It will be appreciated that the method of the present invention can be carried out utilizing two or more separate devices for the scoring step and the dissecting step. That is, a first device having a sharp punch and a second device having a blunt punch can be used to dissect and extract the follicular unit.

However, in a preferred embodiment, the method is carried out using a single device that incorporates both the sharp scoring punch and the blunt dissecting punch. For example, the device can include a sharp punch disposed at one end of a rigid handle and a dissecting blunt punch at the other end of the handle.

FIG. 3 illustrates such a device according to one embodiment of the present invention. The device includes a sharp scoring punch 314 for scoring the skin layers, as is described above. The sharp scoring punch 314 can have an outer diameter as is described with respect to FIG. 2, and in one embodiment has an outer diameter of about 1 mm.

Figure 5:
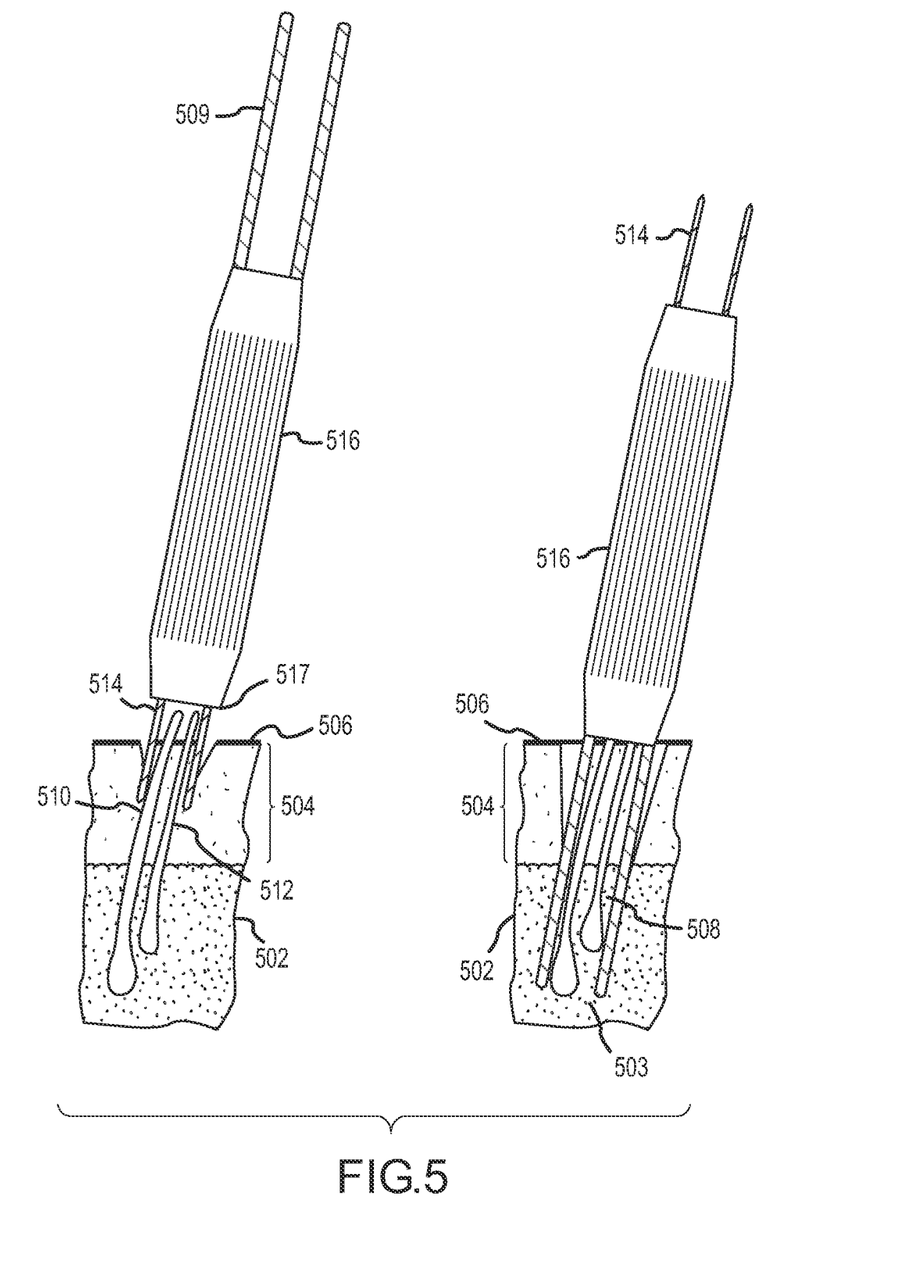
FIG. 5 illustrates a follicular extraction device and method according to an embodiment of the present invention.

In the embodiment illustrated in FIG. 3, the sharp scoring punch 314 is disposed within the lumen of an outer blunt dissecting punch 315. The operator aligns the device, specifically the scoring punch 314, approximately parallel to the hairs 310 and 312 protruding from the epidermis, such that the protruding hairs 310 and 312 are disposed within the lumen of the sharp scoring punch 314. The device, with the sharp scoring punch 314 extended, sharply cuts through the epidermis 306 and scores the upper dermis 304, preferably to a total depth of not greater than about 1.5 mm, such as from about 0.3 mm to about 1.5 mm, the depth of the incision preferably being limited by the device (FIG. 3(a)). As is illustrated in FIG. 3, the incision depth of the scoring punch 314 is limited by the end of the dissecting punch 315. The sharp scoring punch 314 is then retracted into the lumen of the dissecting punch 315, and the dissecting punch 315 is advanced into the score created by the scoring punch and through the dermis 304 and into the fatty layer 302, preferably to a depth as discussed above with respect to FIG. 2, such as from about 4 mm to about 7 mm (FIG. 3(b)). The insertion depth of the dissecting punch is also preferably limited to the preferred depths disclosed herein by the device. As is illustrated in FIG. 3(b), the insertion depth of the dissecting punch is limited by the end of the housing enclosing the scoring punch 314 and dissecting punch 315. The housing can also serve as the handle of the device to be gripped by the operator, as is illustrated in the embodiment of FIG. 5.

Figure 3A:
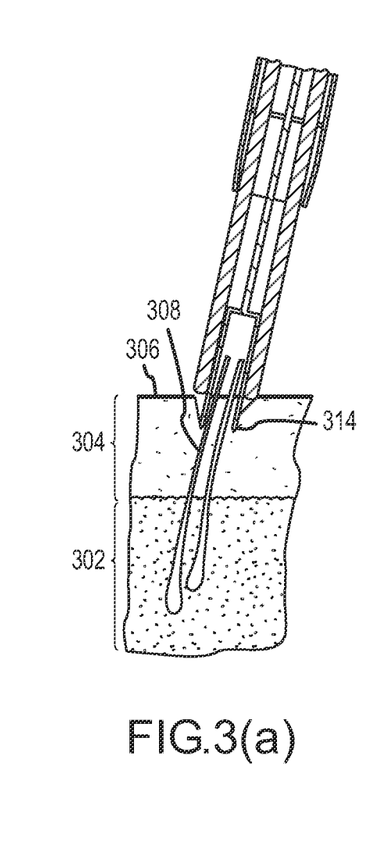
FIG. 3 illustrates a follicular extraction device and method according to an embodiment of the present invention.
Figure 3B:
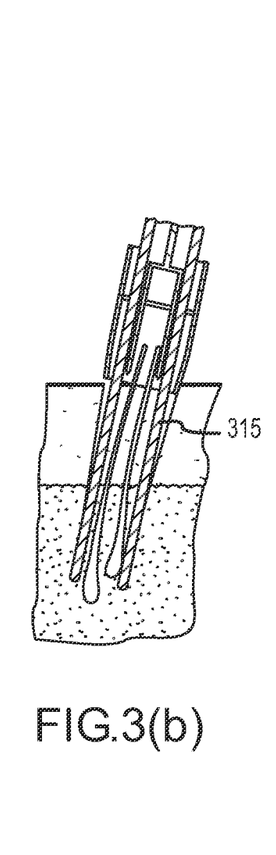
Figure 3C:
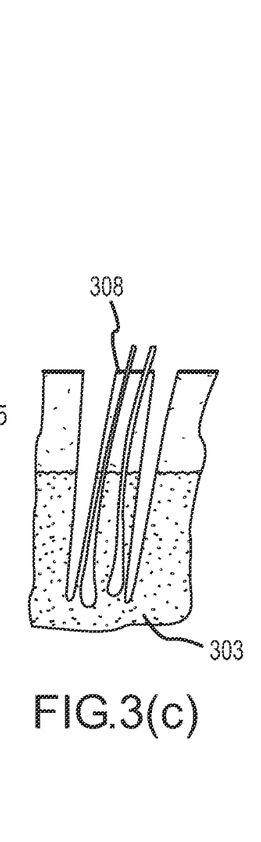
Figure 3D:
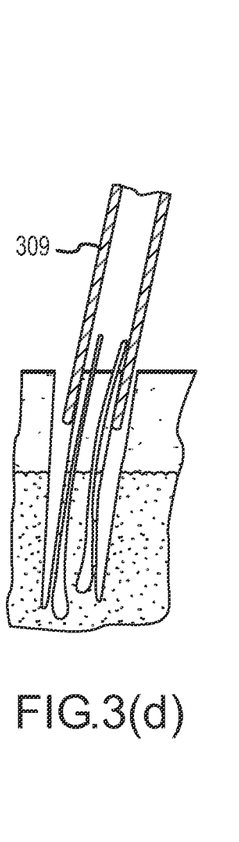
Figure 3E:
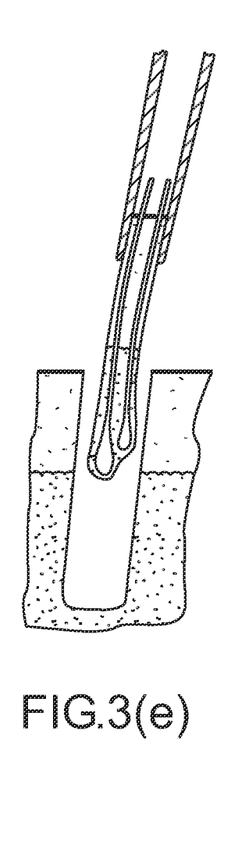
Figure 4A:
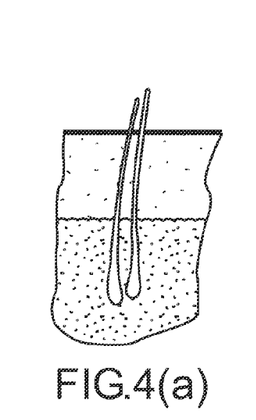
FIG. 4 illustrates a follicular extraction device and method according to an embodiment of the present invention.
Figure 4B:
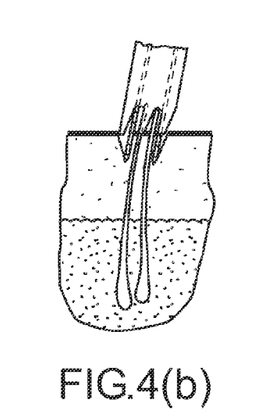
Figure 4C:
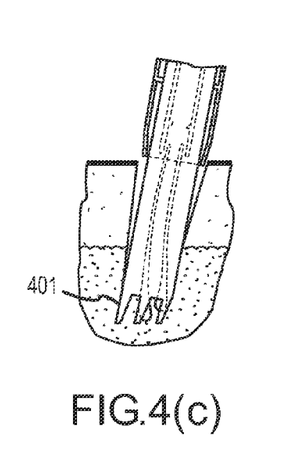
Figure 4D:
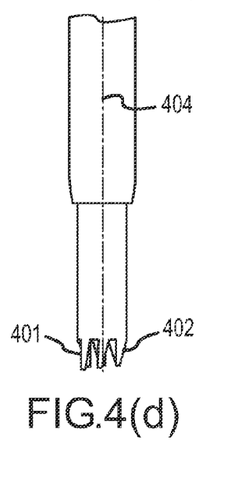
Figure 4E:
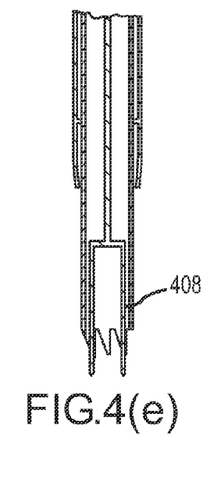
Figure 4F:
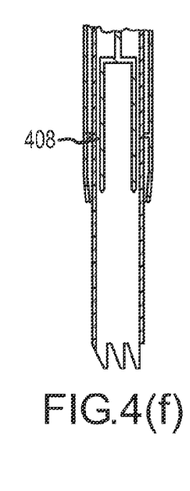
Figure 4G:
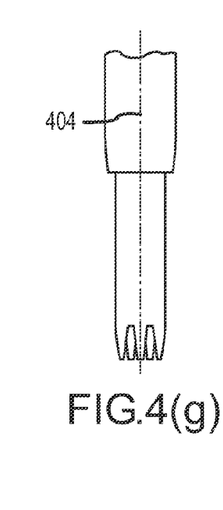

The action of the dissecting punch 315 bluntly separates the fibrous attachments surrounding the follicular unit 308, leaving it attached only at its base 303 (FIG. 3(c)). The operator then removes the follicular unit 308 from the skin using forceps 309, or a similar device (FIGS. 3(d) and 3(e)), such as a tension device or a suction device, for example. The follicular unit is then ready for implantation at the recipient site.

FIG. 4 illustrates a preferred embodiment of the present invention where the dissecting punch utilizes a serrated or "saw tooth" tip 401 comprising a plurality of splines. This modification allows the dissecting punch to more readily separate the attachments of the dermis to the follicular unit and allow advancement through the tissues with greater ease by using rotation, either manual rotation or automated rotation. Any number of splines 402 can be utilized and in one embodiment, the dissecting punch tip includes from 2 to 5 splines. One edge of the splines may be at an angle relative to the primary axis 404 of the dissecting punch, as illustrated in FIGS. 4(b), 4(c), 4(d), 4(e) and 4(f), or straight (substantially parallel to the primary axis 404 of the dissecting punch) as illustrated in FIG. 4(g). FIG. 4(d) shows the external appearance of the dissecting punch while FIGS. 4(e) and 4(g) represent a cross section of this modified dissecting punch tip showing a scoring punch 408 extended and retracted respectively.

It should also be noted that according to one embodiment the scoring punch and dissecting punch could be one in the same. More specifically, a single punch can include a number of splines that have a sharp leading edge and are capable of scoring the skin when rotated in one direction, and having a blunt trailing edge that is capable of dissecting without transecting the hair follicles when the punch is rotated in the opposite direction.

According to one embodiment, either a suction probe within the lumen of the device or mechanical forceps provide traction on the follicular unit in order to remove the follicular unit. Further, the device can include a mechanism for rotating the sharp scoring punch and/or dissecting punch as they are pressed into the patient's skin. Another embodiment includes a mechanism whereby a blade or biting scoop or dissecting wire is incorporated into the tip of the dissecting punch, and when activated will sever the fatty attachment at the base of the follicular unit to enhance the ease of plug removal from the surrounding skin. This modification may or may not include a method to remove the follicular unit in its entirety through the lumen of the device using mechanical grasping or suction application to the follicular unit, such as to move the follicular unit to a chilled holding solution.

FIG. 5 illustrates a follicular extraction device according to another embodiment of the present invention. The device includes a rigid handle 516, preferably made of medical grade plastic or other suitable material that can have a scored surface to promote the ease of handling. At one end, the device includes a sharp scoring punch 514 shown in cross-section for scoring the skin layers, as is described above. The sharp scoring punch 514 can have an outer diameter as is described with respect to FIG. 2, and in one embodiment has an outer diameter of approximately 1 mm. A blunt dissecting punch 509, shown in cross-section, is provided at the other end of the device and preferably has an inner diameter of from about 0.8 mm to about 1.0 mm. The leading edge of the dissecting punch 509 is less sharp than the scoring punch 514 so that the probability of shearing a hair follicle is very low.

The user can align the device, specifically the scoring punch 514, approximately parallel to the hairs 510 and 512 protruding from the epidermis such that the protruding hairs are disposed within the lumen of the sharp scoring punch 514. The device, held between the fingers, is rotated about the axis of the handle and sharply cuts through the epidermis 506 and scores the upper dermis 504, preferably to a total depth of from about 0.3 mm to about 1.5 mm, the depth of the incision preferably being limited by the device. In the embodiment illustrated in FIG. 5, the depth is limited by a lower surface 517 of the handle 516. The device is then rotated or "twirled" between the operator's fingers so that the dissecting punch 509 is in position over the protruding hairs 510 and the incised epidermis 506 and dermis 504. The dissecting punch is then advanced through the dermis 504 and the fatty layer 502, preferably to a depth as discussed above with respect to FIG. 2, such as from about 4 mm to about 7 mm, the depth preferably being limited by the device. This action bluntly separates the fibrous attachments surrounding the follicular unit 508, leaving it attached only at its base 503. The tip of the dissecting punch can also be serrated, as is described above and is illustrated in FIG. 4(f) and FIG. 4(g).

The operator can then remove the follicular unit 508 from the skin using forceps 509, or a similar device. The follicular unit is then ready for implantation at the recipient site. The process can be repeated multiple times to affect the proper number of follicular unit extractions.

Figure 6:
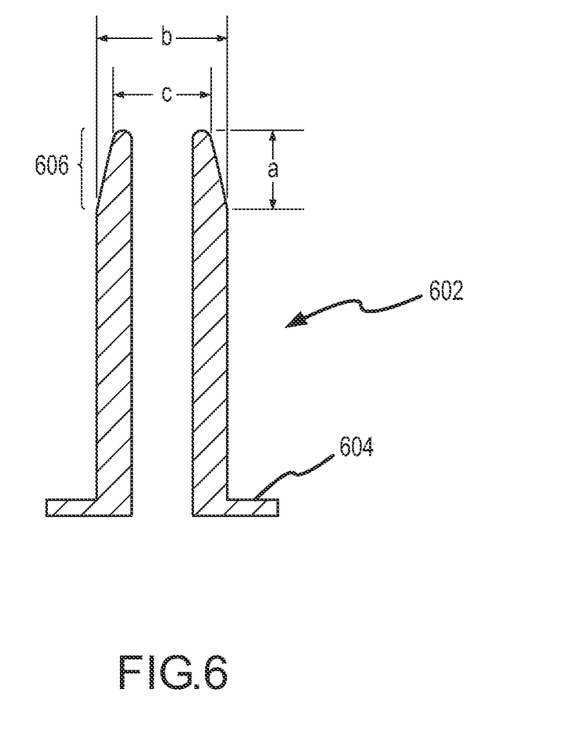
FIG. 6 illustrates the dissecting punch of a follicular extraction device according to an embodiment of the present invention.

According to one preferred embodiment of the present invention, the dissecting punch is tapered (e.g., beveled) to ease insertion of the punch into the scored skin. A cross-section of such a dissecting punch is illustrated in FIG. 6. The punch 600 includes a blunt dissecting tip 602 and a shoulder 604 adapted to restrict the penetration depth of the punch. The punch includes a tapered portion 606 to ease insertion of the punch and to enhance the separation of the follicular unit from the surrounding skin tissue. It will be appreciated that a taper can be applied to a non-serrated punch as well as a serrated punch. According to one embodiment, the length of the tapered portion (a) is at least about 0.3 mm and is not greater than about 0.7 mm. According to a more preferred embodiment, the tapered portion has a length of at least about 0.4 mm and not greater than 0.6 mm, such as about 0.5 mm. For efficient dissection, the tapered portion 606 preferably reduces the primary outside diameter by at least about 10% and not greater than about 30%, such as by about 20%. For example, in one embodiment the punch 600 has a primary outer diameter (b) of about 1.52 mm and a tip diameter (c) of about 1.24 mm, where the total length of the dissecting punch (e.g., to the shoulder 604) is about 5 mm and the inner diameter is about 1 mm.

Figure 7:
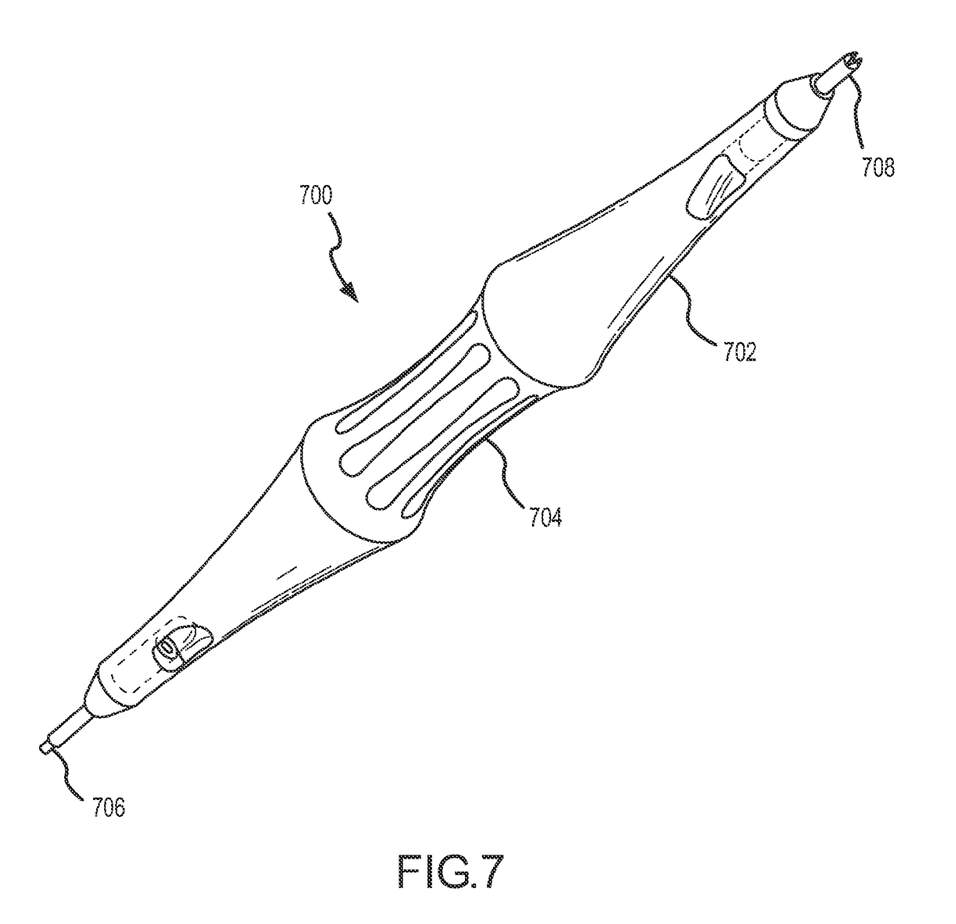
FIG. 7 illustrates a perspective view of a follicular extraction device according to an embodiment of the present invention.

FIG. 7 illustrates a perspective view of a follicular extraction device 700 according to another embodiment of the present invention. The device 700 includes an elongated handle 702 having a recessed mid-section 704 adapted to be gripped by a user. A first end of the handle 702 comprises a sharp scoring punch 706 adapted to score the epidermis and dermis of the patient. The device can then be flipped in the operator's hands and the blunt dissecting punch 708 located at a second end of the handle 702 can be used to dissect the follicular unit from the surrounding skin tissue.

Figure 8:
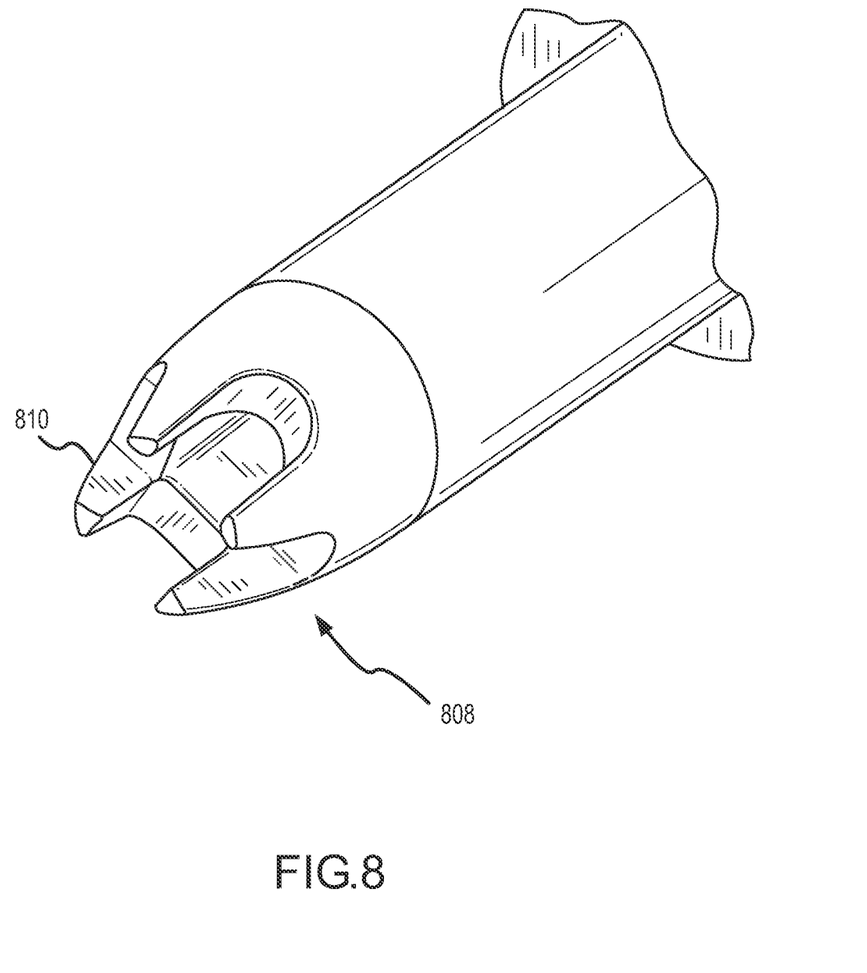
FIG. 8 illustrates close-up perspective view of a blunt dissecting punch according to an embodiment of the present invention.

FIG. 8 illustrates a perspective view of the blunt dissecting punch illustrated in FIG. 7. The blunt dissecting punch 808 includes a tapered portion and is serrated to accommodate removal of the follicular unit from the surrounding skin tissue. As is illustrated in FIG. 8, the blunt dissecting punch includes 4 splines 810.

The foregoing illustrates some devices that are adapted to carry out the method of the present invention. However, it will be appreciated by those skilled in the art that the method can be carried out utilizing other devices.

EXAMPLES

The method of the present invention is carried out to perform follicular extraction on a number of patients. Testing includes patients with demanding hair types, African Americans and those with gray hair, and the results are substantially zero transaction on a limited number of samples. Extrapolation of timing trials using the method of the present invention reveals the ability to extract 300 to 400 grafts per hour. This rate of graft production may convey the ability to transplant up to 2000 grafts per day. A device combining multiple components has the potential to double this graft production rate and allow cases of up to 3000 grafts per day.

The serrated dissecting punch according to the present invention can reduce the frequency of buried follicular units, a phenomenon where the dissecting punch pushes the follicular unit into the skin tissue. In another example, three patients are enrolled in a follicular extraction procedure, receiving a total of 422 grafts. The method of the present invention is utilized wherein a sharp dissection of the epidermis is made with a 1 mm punch (Miltex, Inc., Bethpage, N.Y.) to a depth of about 1.3 mm followed by the insertion of a blunt serrated dissecting punch (similar to that illustrated in FIG. 8) to a depth of 5 mm. The follicular units are then removed with Foerster forceps. Follicular transaction rates and the incidents of buried follicular units are recorded.

The grafts represent a possible total of 1207 follicles, with 48 follicles transected. This is a follicular transaction rate of 4 percent. In this series of 422 extracted grafts, there are 4 buried grafts with 3 retrieved, representing a graft burial rate of 0.9% and a non-retrieval rate of 0.2%. The serrated tip allows for a more rapid and smoother insertion process that enhances the dissection process.

While various embodiments of the present invention have been described in detail, it is apparent that modifications and adaptations of those embodiments will occur to those skilled in the art. However, is to be expressly understood that such modifications and adaptations are within the spirit and scope of the present invention.

What is claimed is:

1. A method for the extraction of a follicular unit from a donor area, comprising the steps of:
    scoring a portion of a donor area with a sharp scoring punch to form a scored incision having a first depth;
    inserting a blunt dissecting punch that is less sharp than the scoring punch into said scored incision to a second depth that is greater than said first depth to dissect tissue to separate a follicular unit for removal from the donor area, wherein said blunt dissecting punch comprises a dissecting distal tip and a lumen at the dissecting distal tip; and
    wherein the sharp scoring punch is disposed within the blunt dissecting punch lumen.

2. The method as recited in claim 1, wherein said dissecting distal tip is serrated.

3. The method recited in claim 1, wherein said scored incision is substantially circular.

4. The method recited in claim 1, wherein said scored incision has a diameter of from about 0.1 mm to about 1.1 mm.

5. The method recited in claim 1, wherein said scored incision has a diameter of from about 0.7 mm to about 1 mm.

6. The method recited in claim 1, wherein said first depth is not greater than about 1.5 mm.

7. The method recited in claim 1, wherein said first depth is from about 0.3 mm to about 1.5 mm.

8. The method recited in claim 1, wherein said second depth is from about 1.5 mm to about 8 mm.

9. The method recited in claim 1, wherein said second depth is from about 4 mm to about 7 mm.

10. The method recited in claim 1, wherein said blunt dissecting punch is removed from the donor area before the follicular unit is removed from the donor area.

11. The method recited in claim 1, further comprising removing the follicular unit from the donor area.

12. The method recited in claim 11, wherein said removing step comprises using suction or removing the follicular unit using forceps.

13. The method recited in claim 11, further comprising the step of separating a bottom portion of said follicular unit from a fatty layer of the donor area before said removing step.

14. The method recited in claim 11, wherein said removing step comprises removing said follicular unit at least in part by applying a force to a top end of said follicular unit.

15. The method recited in claim 1, wherein said inserting step comprises rotating said blunt dissecting punch about a primary axis of said blunt dissecting punch.

16. The method recited in claim 1, further comprising the step of transplanting said follicular unit.

17. The method recited in claim 1, wherein said dissecting distal tip comprises an outer diameter that is tapered.

18. The method recited in claim 1, wherein said dissecting distal tip comprises a rounded annular dissecting edge.

19. The method recited in claim 1, wherein at least one of said scoring step and said inserting step is mechanized.

20. The method recited in claim 1, wherein said blunt dissecting punch lumen has an inner diameter of from about 0.8 mm to about 1.0 mm.

21. The method recited in claim 1, wherein said inserting step comprises advancing said dissecting distal tip through a dermis and into a fatty layer of said donor area.

22. The method recited in claim 1, wherein said inserting step separates fibrous attachments surrounding said follicular unit to leave said follicular unit attached to a fatty layer of the donor area at its base.

23. The method recited in claim 1, further comprising limiting a depth of insertion of at least one of said sharp scoring punch and said blunt dissecting punch.

24. A method for the extraction of a follicular unit from a donor area, comprising the steps of:
    scoring a portion of a donor area with a sharp scoring punch to form a scored incision having a first depth of not greater than about 1.5 mm;
    inserting a blunt dissecting punch that is less sharp than said scoring punch into the scored incision to a second depth of at least about 4 mm to facilitate removal of a follicular unit, said blunt dissecting punch comprising a distal annular dissecting edge that forms a lumen, wherein the sharp scoring punch is disposed within the blunt dissecting punch lumen; and
    making an incision in a recipient area to transplant said follicular unit in the recipient area.

25. The method recited in claim 24, further comprising removing said follicular unit at least in part by applying a force to a top end of said follicular unit.

26. The method recited in claim 24, further comprising removing said follicular unit using forceps.

27. The method recited in claim 24, wherein an outer diameter of said blunt dissecting punch proximate to said distal annular dissecting edge is tapered.

28. The method recited in claim 24, wherein said distal annular dissecting edge is rounded.

29. The method recited in claim 24, wherein at least one of said scoring step and the inserting step is mechanized.

30. The method recited in claim 24, further comprising limiting a depth of insertion of at least one of said sharp scoring punch and said blunt dissecting punch.

31. The method recited in claim 24, wherein said blunt dissecting punch lumen has an inner diameter of from about 0.8 mm to about 1.0 mm.

32. The method recited in claim 24, wherein said inserting step comprises advancing said distal annular dissecting edge through a dermis and into a fatty layer of said donor area.

33. The method recited in claim 24, wherein said inserting step separates fibrous attachments surrounding said follicular unit to leave said follicular unit attached to a fatty layer of the donor area at its base.

34. A method for the extraction of a follicular unit plug from a donor area, comprising the steps of:
    penetrating a portion of a donor area with a sharp scoring punch to form an incision having a first depth;
    advancing a blunt distal tip of a blunt dissecting punch through the incision to a second depth that is greater than said first depth and forming a follicular unit plug comprising a follicular unit, the blunt dissecting punch comprising a lumen at said blunt distal tip and wherein said blunt distal tip guides the follicular unit plug into said lumen for removal from the donor area; and wherein the sharp scoring punch is disposed within the blunt dissecting punch lumen.

35. The method recited in claim 34, wherein said first depth is not greater than about 1.5 mm.

36. The method recited in claim 35, wherein said second depth is from about 4 mm to about 7 mm.

37. The method recited in claim 34, further comprising removing said follicular unit plug using forceps.

* * * * *